United States Patent [19]
Ashley

[11] Patent Number: 5,664,581
[45] Date of Patent: Sep. 9, 1997

[54] INTRAVENOUS TUBING SECURE STRAP

[76] Inventor: John P. Ashley, 6809 Pine Dr., Chattanooga, Tenn. 37421

[21] Appl. No.: 717,531

[22] Filed: Sep. 17, 1996

[51] Int. Cl.$^6$ .................................................. A61F 5/37
[52] U.S. Cl. ........................... 128/876; 128/877; 604/179
[58] Field of Search ........................... 128/846, 869, 128/874, 875, 876, 877, 878, 879, DIG. 26, DIG. 15; 604/174, 179, 180; 602/41, 61, 62

[56] References Cited

U.S. PATENT DOCUMENTS

| | | | |
|---|---|---|---|
| 3,812,851 | 5/1974 | Rodriguez | 128/133 |
| 4,470,410 | 9/1984 | Elliot | 138/133 |
| 4,569,348 | 2/1986 | Hasslinger | 604/179 |
| 4,671,787 | 6/1987 | Widman | 604/179 |
| 4,702,736 | 10/1987 | Kalt | 604/180 |
| 4,799,923 | 1/1989 | Campbell | 604/179 |
| 4,862,904 | 9/1989 | West | 128/877 |
| 5,037,397 | 8/1991 | Kalt | 604/174 |
| 5,076,289 | 12/1991 | Darling | 128/877 |
| 5,291,903 | 3/1994 | Reeves | 128/878 |
| 5,339,834 | 8/1994 | Marcelli | 128/877 |
| 5,413,120 | 5/1995 | Grant | 128/877 |
| 5,413,562 | 5/1995 | Swauger | 604/174 |

FOREIGN PATENT DOCUMENTS 2273 242  6/1994  United Kingdom .

OTHER PUBLICATIONS

Abott Laboratories, Primary I.V. Pump Set Insert, ©1992.
Dale Foley Catheter Holder Product Sheet, ©1994.

*Primary Examiner*—Michael A. Brown
*Attorney, Agent, or Firm*—Miller & Martin

[57] ABSTRACT

The present invention constitutes a device for securing and restraining intravenous tubing to prevent dislodgment of a venipuncture device. A secure strap according to the present invention utilizes hook and loop fasteners and restrains the movement of a Y injection placed on the intravenous line.

20 Claims, 4 Drawing Sheets

INTRAVENOUS TUBING SECURE STRAP

FIELD OF THE INVENTION

The present invention relates to an infusion secure strap, and more particularly to a new and unique non-adhesive support for intravenous tubing.

BACKGROUND OF THE INVENTION

In many cases, a drip infusion is required to introduce a solution, as of glucose or saline, into the body of a patient through a vein. A drip infusion is commonly introduced into a vein on the back of the hand or on the forearm. The tubing used for the intravenous drip infusion often serves as a convenient vehicle for administering medications. Accordingly, hospital patients are frequently connected to intravenous tubes, both to provide hydrating fluid and to administer therapeutic agents. Because the patients may be connected to the intravenous tubing for several hours or even several days, it is important that the needle or venipuncture device not be inadvertently dislodged.

For securing the venipuncture device to the patient's hand or forearm, adhesive membranes sold under the brandnames TEGADERM or OPSITE are frequently used. These membranes have some adhesive qualities and are typically impregnated with antibacterial agents. However, without additional support, these membranes are insufficient to retain the venipuncture device in place.

The usual solution involves applying layers of adhesive tape to secure the intravenous tubing to the arm of the patient. Typically one application of tape is made near the venipuncture site and another is located more remotely along the patient's arm. This has been less than satisfactory for several reasons. Particularly, adhesive tapes may lose their binding force as the patient perspires or liquids spill on the site. In addition, the adhesives cause irritation to patients, particularly the hirsute, those with sensitivity to adhesive, or some aged patients with thin and brittle skin. Since the intravenous tubing has to be replaced every 48–72 hours, the tape also has to be replaced, thus these discomforts may be substantial over the course of an extended hospitalization. The need exists to provide means to secure intravenous tubing in a method that will protect against the accidental dislodgment of the venipuncture device and at the same time minimize the discomfort and restrictions of utilizing adhesives.

BRIEF SUMMARY OF THE INVENTION

The present invention relates to an intravenous tubing secure strap which is specially adapted to restrict the movement of Y injection ports which are standard on most intravenous lines. The strap includes a base or bed to which are attached both a securing tab that restricts the Y injection port and an overwrap that acts to secure the base on the patient's arm and to more securely limit the mobility of the Y injection port. The wrap is fixed in place by hook and loop fasteners so that it may be easily attached and released intentionally.

Accordingly, it is a primary object of the present invention to provide a new and improved intravenous tubing secure strap for non-adhesively securing intravenous tubing to a patient, thereby avoiding the necessity of shaving patient's arms and the loss of holding force if the securing means should become wet.

It is a further object of the present invention to provide a fast and convenient secure strap for intravenous tubing that is inexpensive and easy to manufacture and provides the patient with greater comfort by not adhering to the hirsute or by tearing weak skin.

An additional object of the present invention is to provide an intravenous tubing secure strap that is usable for venipunctures made either upon the patient's hand or forearm.

It is another object of the present invention to provide a reusable intravenous tubing secure strap.

It is a further object of the present invention to provide a means for securing intravenous tubing that does not restrict the patient's circulation, and that does not have a tendency to cause crimps in the lumen of the tubing.

These and other objects as shall appear in the detailed description are provided by the present invention, particularly when examined in connection with the accompanying drawings.

BRIEF DESCRIPTIONS OF THE DRAWINGS

DETAILED DESCRIPTION

Figure 1:
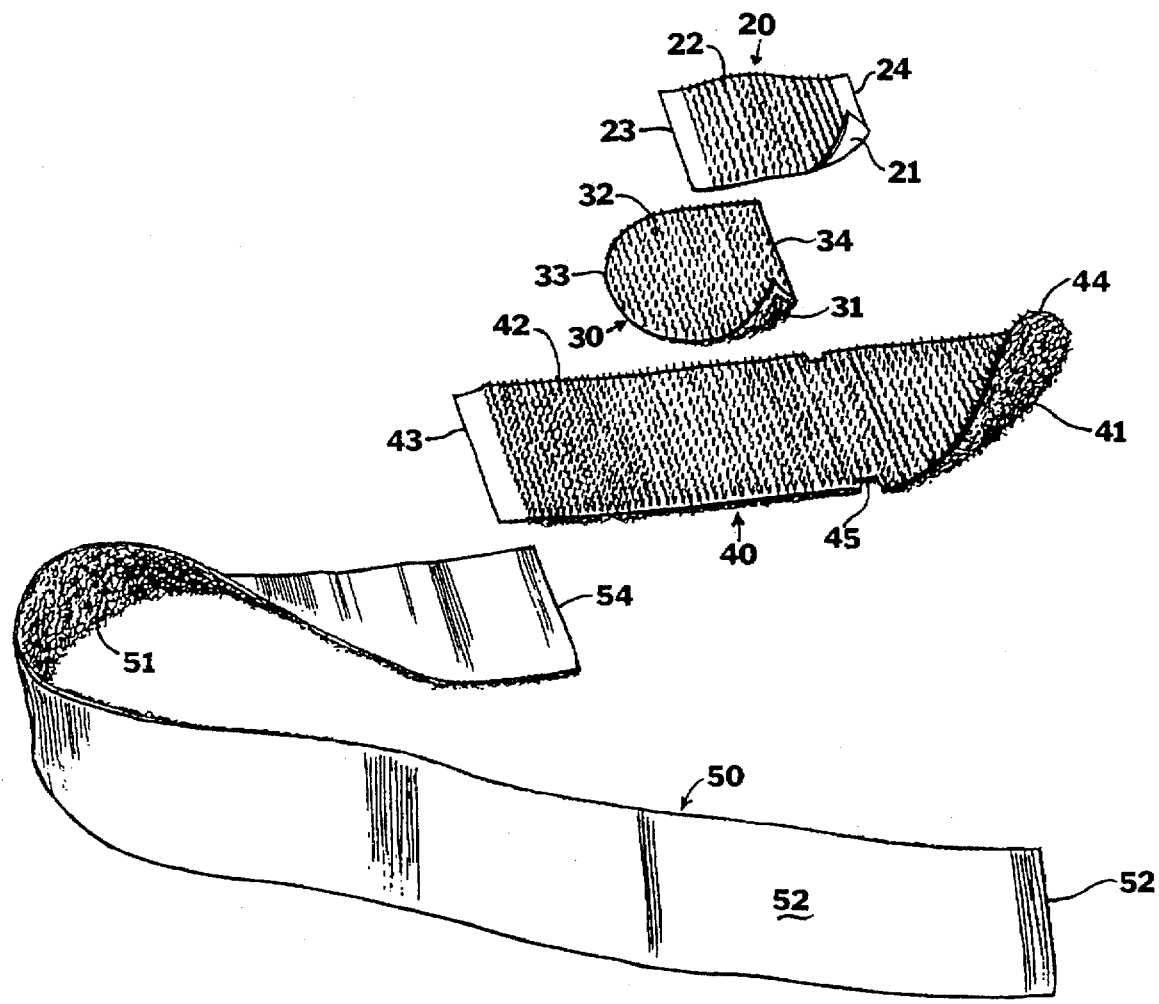
FIG. 1 is an exploded perspective view of the components of an intravenous tubing secure strap made according to the present invention.
Figure 2A:
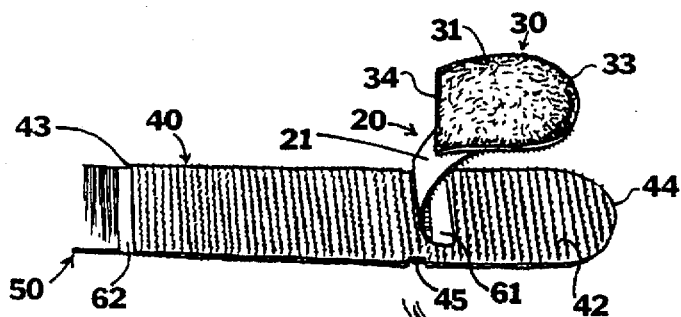
FIG. 2A is a perspective view of the portion of an intravenous tubing secure strap made according to the present invention adapted to restrict movement of the Y injection port of the intravenous line.
Figure 2B:
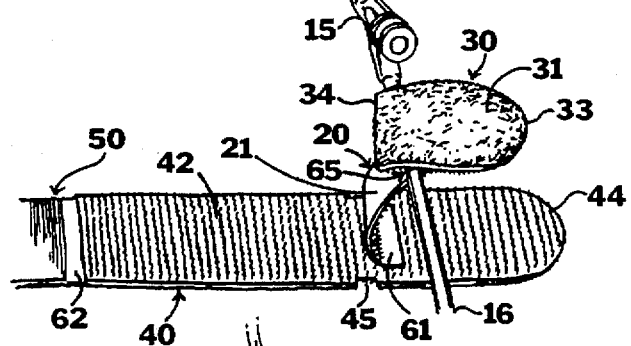
FIG. 2B is a view of the section of 2A showing the positioning of the intravenous tube and Y injection port.
Figure 2C:
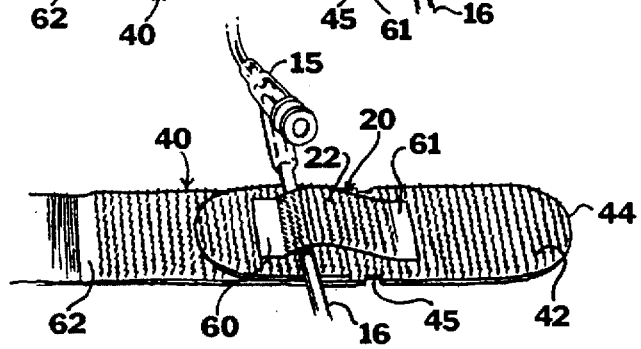
FIG. 2C is a view of the section of 2A showing the encirclement of the intravenous tube.
Figure 2D:
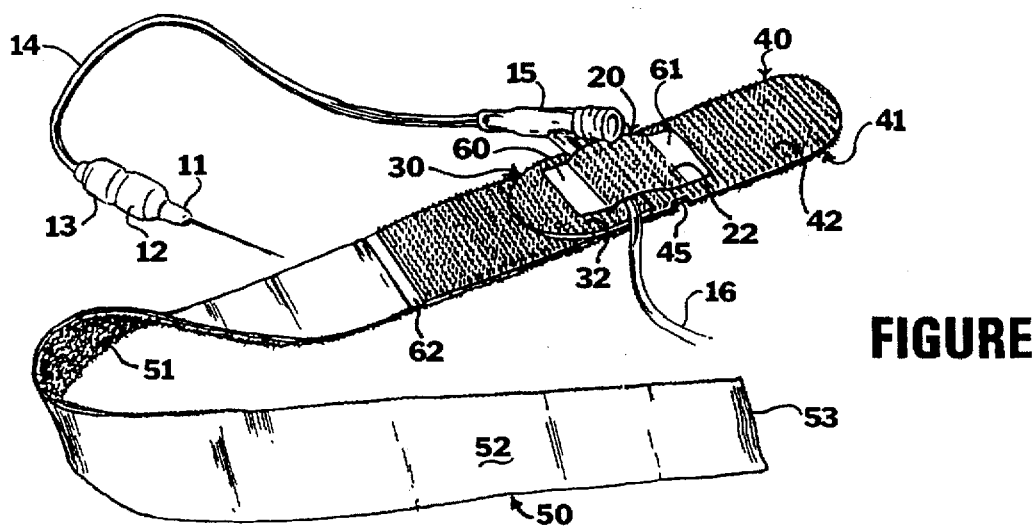
FIG. 2D is a view of an intravenous tubing secure strap according to the present invention with the movement of the Y injection port away from the venipuncture device restricted.

The intravenous tubing securing means of the present invention is shown in it's assembled form in FIG. 2D and as identified by reference 10. The components of the secure strap 10 are best viewed in FIG. 1 in isolation. These components of the preferred construction of the invention include bridge or bridge hinge 20, secure tab 30, and a strap section preferably comprising a bed or base 40 and overwrap 50. The underlying surface 51 of overwrap 50 is preferably a loop material such as that sold by Velcro USA, Inc. under the VELCRO trademark, as a part of its hook and loop fastening systems. The overlying surface 52 of the overwrap is preferably a relatively smooth finished fabric which may be screened with artwork, including manufacturers' and hospitals' logos and advertising. The proximal end 53 of the overwrap 50 remains unattached while the distal end 54 is attached to proximal end 43 of bed 40. The overlying surface 42 of bed 40 is preferably hook fastener material which is adapted to adhere to loop material such as the underlying surface 51 of overwrap 50. The underlying surface 41 of bed 40 is a soft loop material to enhance patient comfort, and which also prevents the Secure strap 10 from sliding too freely on the patient's arm. The distal end 54 of overwrap 50 and proximal end 43 of bed 40 are perferably attached by sonic welding for strength and manufacturing efficiency to form the strap section of the secure strap. The bed 40 also preferably has opposed seating slots 45 which serve to restrain the intravenous tubing line if it slips out of its preferred position as later described. The distal end 44 of bed 40 is rounded without corners that might contribute to patient discomfort.

Attached to the bed 40 toward the distal end 44 of slots 45 is the bridge hinge 20. Distal end 24 of bridge hinge 20 is preferably sonically welded to bed 40. The overside 22 of bridge hinge 20 is of hook material and the underside 21 is preferably a smooth surface. In the preferred embodiment, the bridge hinge 20 is manufactured from a translucent material to provide greater visibility of the intravenous tubing. The smooth underside 21 is preferably a slick laminate to minimize friction against the intravenous tubing.

The proximal end 23 of bridge hinge 20 is attached and preferably sonically welded to the overside 32 of secure tab 30. The overside 32 of secure tab 30 is a hook material and the underside 31 is a loop material. The secure tab 30 in conjunction with bridge hinge 20 forms a station for encircling intravenous tubing. The proximal end 33 of secure tab 30 preferably has rounded corners which facilitates the unfastening of the loop and hook fastening of the secure tab 30 to the base 40 by hospital personnel wearing gloves. Even without rounded corners, the secure tab 30 is much easier for gloved hands to release than tape. Finally, because the secure tab 30 is critical to the proper functioning of the invention, it is preferably a contrasting color from the remainder of the secure strap 10.

Turning now to FIG. 2A, an embodiment of the invention is shown with particular focus on the bed 40, bridge hinge 20, and secure tab 30. Bridge hinge 20 is attached by sonic weld 61 to bed 40 just to the distal side 44 of opposed seating slots 45. The proximal end 23 (as best shown in FIG. 1) of bridge hinge 20 is similarly fastened to secure tab 30. The bed 40 may thus be considered to be divided into three sections: (1) a distal end section between weld 61 and distal end 44; (2) an intermediate encircling section from the fastening position of secure tab 30 on hook overside 42 to weld 61; and (3) a proximal section between proximal end 43 and the point where secure tab 30 is fastened to hook overside 42. Although the bed 40 is preferably about four inches long, it will be seen that the distal end section and proximal section can be relatively short so that the overall length of the bed 40 can be only slightly greater than the intermediate section where the bridge 20 is attached and where the secure tab 30 is fastened.

The first step of utilizing the secure strap 10 is shown in FIG. 2A where the bed 40 is placed on the patient's wrist or forearm and secure tab 30 is bent back away from the bed 40 in an unfastened position. In the second step of utilizing the secure strap 10, as shown in FIG. 2B, intravenous tubing 16 which proceeds from a fluid supply, not shown, to a Y injection port 15 is nestled in a crotch 65 created between the overside 32 of the distal end 34 of secure tab 30 and the underside 21 of bridge hinge 20 on the interior of their attachment at sonic weld 60. This crotch 65 and the area under bridge 20 is a critical functional area of the strap 10 and the length of this area from attachment 60 to attachment 61 should be less than one inch for optimum results.

In the third step shown in FIG. 2C, the loop underside 31 of secure tab 30 (best viewed in FIG. 2B), is fastened to the hook overside 42 of bed 40, thereby encircling intravenous line 16 between bed 40, secure tab 30 and bridge 20. Thus the secure tab 30 has anchored the proximal end 23 of bridge hinge 20 to the bed 40. In conjunction with bridge hinge 20, secure tab 30 forms the station for encapturing the intravenous tubing 16. When tubing 16 is positioned in crotch 65 between secure tab 30 and bridge 20, the tubing 16 cannot work in between secure tab 30 and bed 40 where it might pull apart the hook and loop fasteners. In the event that tubing 16 should not be properly lodged in crotch 65, seating slots 45 on bed 40 will tend to hold the tubing in a safe position.

It will be noted that although the intravenous tubing 16 is encaptured in the third step, the lumen of the tubing is not restricted or crimped and some longitudinal movement of the intravenous tubing 16 is possible so long as the Y injection port 15 remains on the same side of the secure strap 10 as the venipuncture device 11.

FIG. 2D shows the Y injection port 15 pulled snugly against bridge hinge 20 and distal intravenous tubing 14 proceeding to male adapter 13. Typically the length of the distal section 14 of intravenous tubing between the venipuncture device 11 and Y-injection port 15 would be approximately 10 to 12 inches. Venipuncture device 11 and female adapter 12 are connected to adapter 13. The venipuncture device 11 would generally be inserted into a patient's vein prior to utilization of Secure strap 10.

Figure 3A:
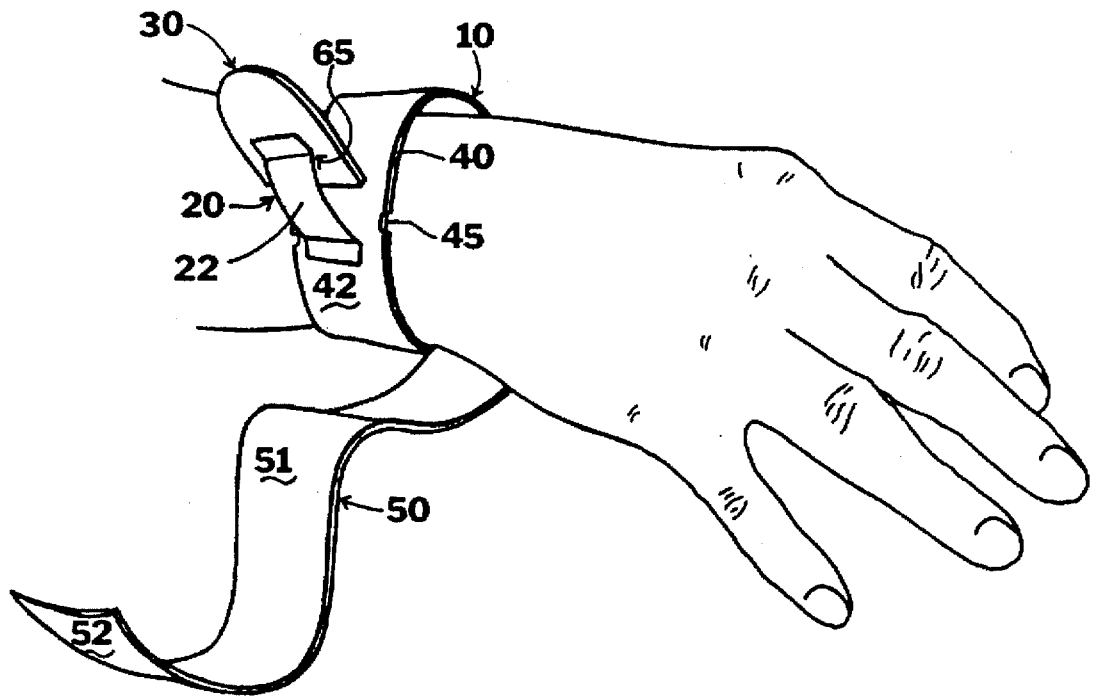
FIG. 3A is an isometric view of an intravenous tubing secure strap according to the present invention at the first step of installing the strap.

Accordingly, in FIG. 3A the secure strap 10 is shown in its first step of deployment, corresponding generally to position shown in FIG. 2A. At this point, the venipuncture device is typically already in place on the patient's hand or forearm. For illustrative purposes, the venipuncture device shown in FIGS. 3A–3E is on the patient's hand. The bed 40 of secure strap 10 is placed with its underside 41 (shown in FIG. 1) on the patient's forearm and overwrap 50 encircles the patient's wrist until the loop underside 51 of the overwrap can engage the hook overside 42 of the distal end 44 of the bed 40 and gently secure the secure strap in place. The bed 40 and overwrap 50 comprise the strap section and are preferably about one inch wide, for patient comfort, to minimize the possibility of crimping the tubing 16, and for adequate strength, though widths as little as one-half inch may be satisfactory.

Figure 3B:
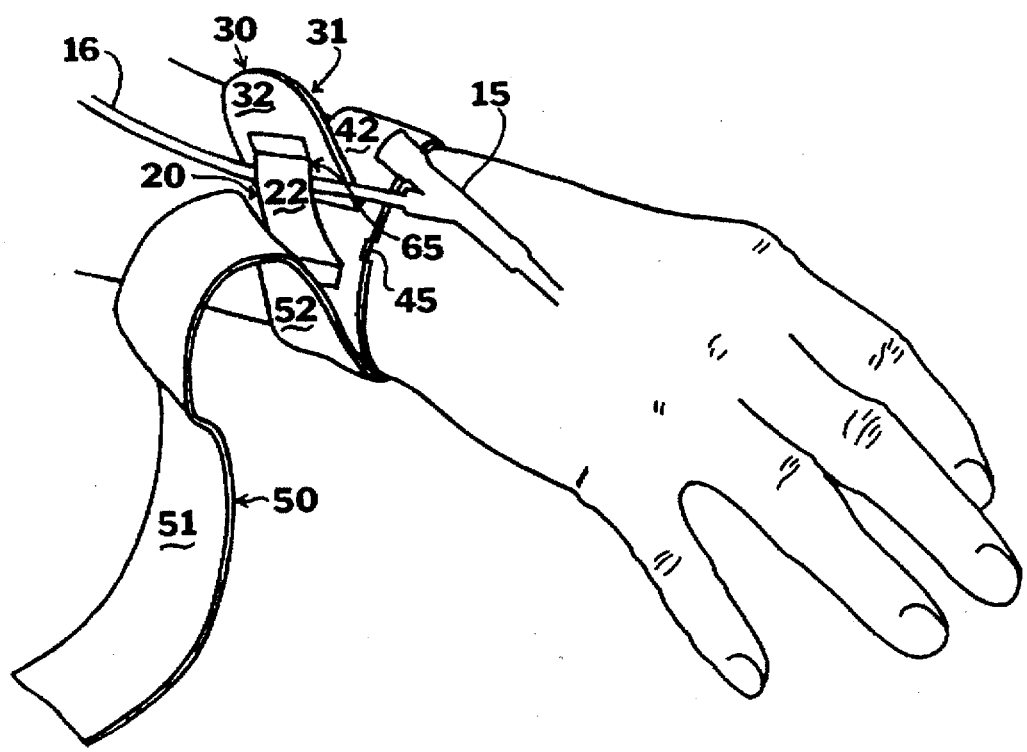
FIG. 3B is an isometric view of an intravenous tubing secure strap according to the present invention at the second step of installing the strap.
Figure 3C:
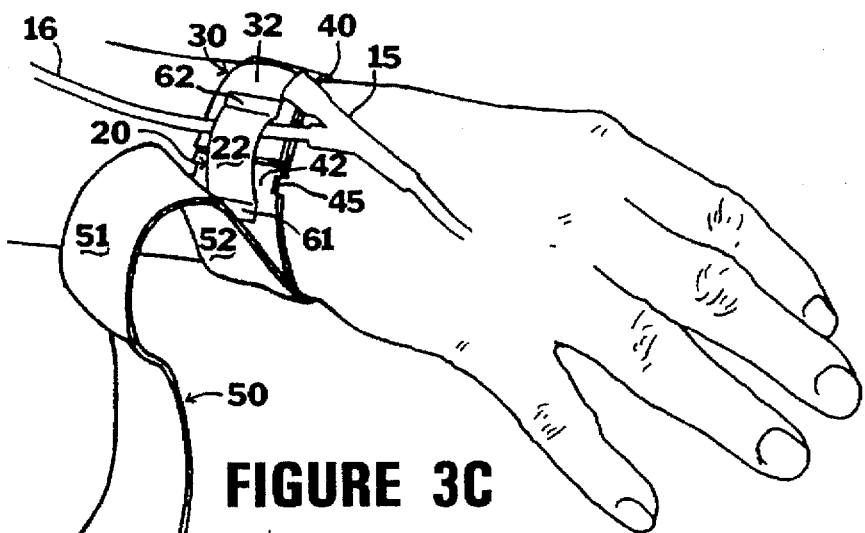
FIG. 3C is an isometric view of an intravenous tubing secure strap according to the present invention at the third step of installing the strap.
Figure 3D:
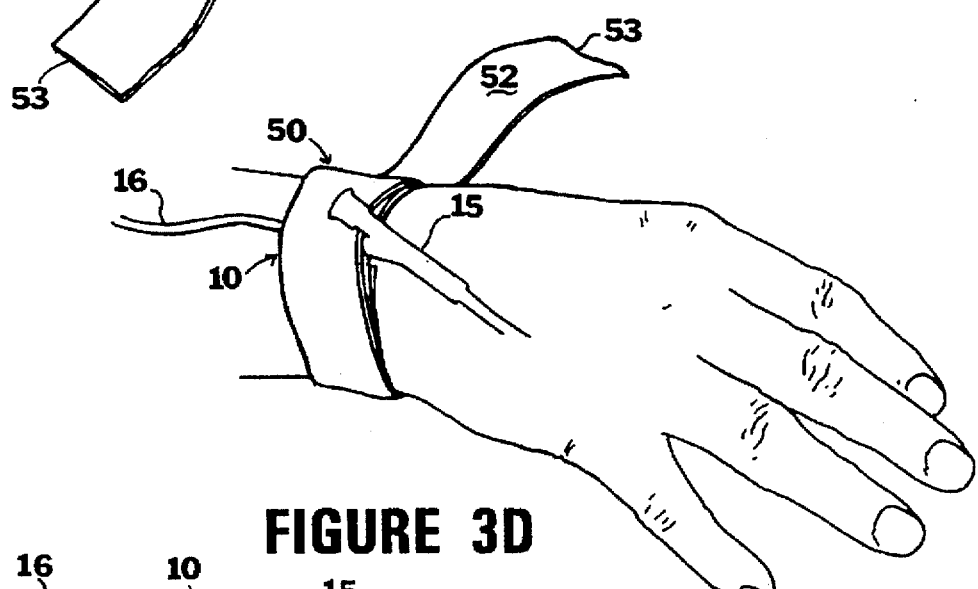
FIG. 3D is an isometric view of an intravenous tubing secure strap according to the present invention at the fourth step of installing the strap.

In FIG. 3B, the intravenous tubing 16 is nestled in the crotch 65 formed between secure tab 30 and bridge hinge 20 as explained in connection with FIGS. 2B and 2C. Then in FIG. 3C, the underside 31 (shown in FIG. 3B) of secure tab 30 has been attached to the loop overside 42 of bed 40. In the fourth step shown in FIG. 3D, overwrap 50 is placed over and covers the remainder of bed 40, bridge hinge 20 and secure tab 30. The overside 22, 32, 42 of each of these elements, 20 30 40, is a hook fastener surface which secures to the loop fastener underside 51 of overwrap 50. If overwrap 50 extends past the proximal end 43 of base 40 and the hook fastener section on the overside 42 thereof, the excess overwrap 50 may be cut off, loosely wrapped as shown in FIGS. 3D and 3E, or alternatively the proximal end 53 may be manufactured with an adhesive segment on the underside to secure the wrap or the overwrap 50 may be wrapped with tape.

Figure 3E:
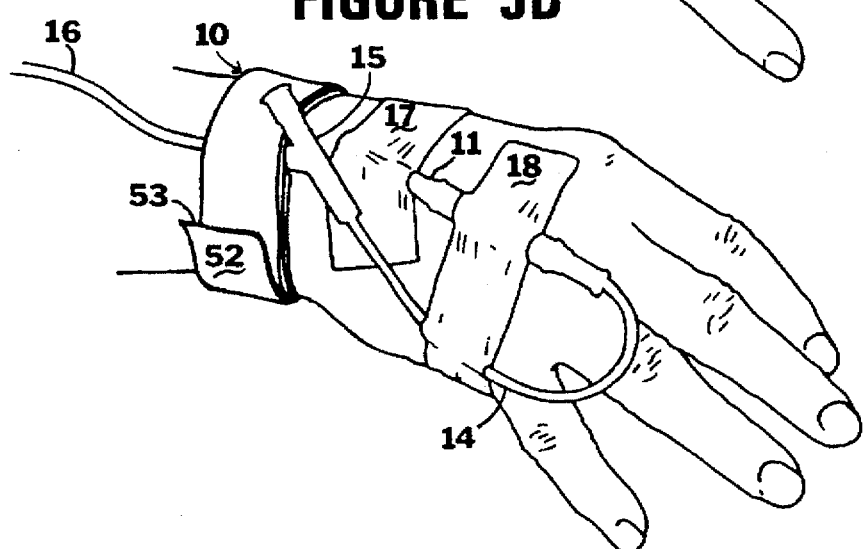
FIG. 3E is an isometric view of an intravenous tubing secure strap according to the present invention shown in its final attached position.

FIG. 3E shows secure strap 10 according to the present invention in place on patient's arm. It will be seen that pulling on intravenous tubing 16 will not cause any pressure to be placed on the venipuncture device 11 because Y injection port 15 cannot be pulled through secure strap 10. Also shown in FIG. 3E is a piece of regular adhesive tape 18 that may still need to be employed in certain cases. Another feature illustrated in FIG. 3E is the anti-bacterial impregnated membrane 17 utilized to hold the venipuncture device 11 in place. The materials used for the construction of the secure strap 10 should be selected for fabrication, as by sonic welding, although other means of attachment such as sewing and gluing are possible. In addition, it is preferred that the materials be non-elastic so that there is no restriction of the patient's blood flow. The overall length of the arm encircling strap section of secure strap 10 from proximal end 53 of overwrap 50 to distal end 44 of bed 40 has been optimized at about 17 inches. It will be understood that this length may vary several inches longer or shorter depending upon the particular applications for which the strap 10 is used.

Numerous alterations of the structures herein described will suggest themselves to those skilled in the art. It will be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. An intravenous tubing secure strap having a tubing encircling portion and an arm encircling portion wherein said arm encircling portion comprises a strap section having an underside and an opposed overside, and a distal end and a proximal end; the overside of the distal end of said strap section having a hook fastener surface, and the underside of said strap section having a soft surface, at least a portion of which is loop fastener surface positioned to fasten with the overside hook fastener surface when the strap section encircles a patient's limb;

and wherein the tubing encircling portion comprises a bridge having a first end attached to the strap section overside hook fastener surface, and having a second end attached to an overside of a secure tab, said secure tab having an underside comprising a loop fastener surface whereby the secure tab loop fastener surface can be fastened to the strap section overside hook fastener surface to encircle a segment of intravenous tubing.

2. The intravenous tubing secure strap of claim 1 wherein the strap section is fabricated from a non-elastic material.

3. The intravenous tubing secure strap of claim 1 wherein the bridge has a length from the attachment of its first end to the strap section overside extending to the attachment of its second end to the secure tab of less than about one inch.

4. The intravenous tubing secure strap of claim 1 wherein the first end of the bridge is attached to the strap section overside, and the second end of the bridge is attached to the secure tab, by sonic welding.

5. The intravenous tubing secure strap of claim 1 wherein the proximal end of the strap section forms a surface to receive printing.

6. The intravenous tubing secure strap of claim 1 wherein the distal end of the strap section is rounded and wherein at least a portion of the underside of the strap section near the distal end has a soft surface.

7. The intravenous tubing secure strap of claim 1 wherein the underside of the proximal end of the strap section has an adhesive surface.

8. The intravenous tubing secure strap of claim 1 wherein the overside of the secure tab comprises a hook fastener surface.

9. The intravenous tubing secure strap of claim 1 wherein the strap section has opposed seating slots immediately proximal to the attachment of the bridge to the strap section overside.

10. An intravenous tubing secure strap comprising:
   (a) a strap section having a first underside and a second opposed overside, and having a distal end and a proximal end, and wherein at least a portion said overside comprises hook fasteners and at least a portion of said underside comprises loop fasteners adapted to engage said overside hook fasteners when the strap section is positioned around a patient's arm;
   (b) a bridge having an underside and an opposed overside, and having a distal end attached to the overside of said strap section, and a proximal end;
   (c) a secure tab having a distal end, a proximal end, an underside at least a portion of which comprises loop fasteners, and an opposed overside attached to the proximal end of said bridge, such that the secure tab overside intermediate the distal end and the bridge, together with the underside of the bridge form a crotch; and wherein the underside loop fasteners of the secure tab are adapted to fasten to at least a portion of the strap section overside hook fasteners.

11. The intravenous tubing secure strap of claim 10 wherein the strap section is fabricated from a non-elastic material.

12. The intravenous tubing secure strap of claim 10 wherein the bridge has a length from the attachment of its distal end to the overside of the strap section to the attachment of its proximal end to the overside of the secure tab of less than about one inch.

13. The intravenous tubing secure strap of claim 10 wherein the distal end of the bridge is attached to the strap section overside and the proximal end of the bridge is attached to the secure tab, by means of sonic welding.

14. The intravenous tubing secure strap of claim 10 wherein the strap section further comprises a distal bed and a proximal overwrap wherein the overside of said bed comprises hook fasteners and the underside of said overwrap comprises loop fasteners.

15. The intravenous tubing secure strap of claim 14 wherein the overside of the overwrap forms a surface to receive printing.

16. The intravenous tubing secure strap of claim 10 wherein the distal end of the strap section is rounded and wherein at least a portion of the underside of the strap section near said distal end has a soft surface.

17. The intravenous tubing secure strap of claim 10 wherein the underside of the proximal end of the strap section has an adhesive surface.

18. The intravenous tubing secure strap of claim 10 wherein the overside of the secure tab comprises a hook fastener surface.

19. The intravenous tubing secure strap of claim 10 wherein the strap section has opposed seating slots immediately proximal to the attachment of the distal end of the bridge to the strap section overside.

20. A method of securing a section of intravenous tubing having a distal end with a venipuncture device and a Y-injection port, and having a proximal end, by applying a secure strap having a strap section with a distal end and a proximal end, a bridge, and a secure tab, comprising the steps of:

(a) positioning an underside of the distal end of strap section on a patient's arm so that an opposed overside of the strap section having a hook fastening surface is exposed;

(b) encircling the patient's arm with the strap section so that a loop fastening section on the underside of the strap section is fastened to said exposed hook fastening surface;

(c) positioning the bridge which has a distal end attached to the overside of the strap section, and a proximal end attached to an overside of the secure tab, so that said bridge extends outwardly away from the strap section encircling the patient's arm;

(d) forming a crotch between an underside of the proximal end of the bridge and the overside of the secure tab;

(e) positioning the intravenous tubing proximal to the Y-injection port in the crotch formed by the bridge and secure tab;

(f) fastening a loop fastener underside of the secure tab to the exposed hook fastening surface of the strap section overside.

* * * * *